United States Patent [19]

Weber et al.

[11] Patent Number: 5,391,484
[45] Date of Patent: Feb. 21, 1995

[54] PROCESS FOR THE PRODUCTION OF 4-PREGNENE-3,20-DIONE AND ITS DERIVATIVES USING MYCOBACTERIUM NRRL B-3805

[75] Inventors: Alfred Weber; Mario Kennecke, both of Berlin, Germany

[73] Assignee: Schering Aktiengesellschaft, Berlin, Germany

[21] Appl. No.: 861,807
[22] PCT Filed: Jul. 30, 1991
[86] PCT No.: PCT/DE91/00620
§ 371 Date: Jun. 18, 1992
§ 102(e) Date: Jun. 18, 1992
[87] PCT Pub. No.: WO92/03571
PCT Pub. Date: Mar. 5, 1992

[30] Foreign Application Priority Data

Aug. 18, 1990 [DE] Germany ............... 4026464

[51] Int. Cl.⁶ .............. C12P 33/04; C12P 33/02; C12P 35/02
[52] U.S. Cl. .............. 435/61; 435/52; 435/253.1; 435/863; 435/148
[58] Field of Search ............ 435/61, 52, 253.1, 863

[56] References Cited

U.S. PATENT DOCUMENTS

| | | | |
|---|---|---|---|
| 2,874,172 | 2/1959 | Herzog et al. | 435/61 |
| 2,905,592 | 9/1959 | Shull et al. | 435/61 |
| 3,102,080 | 8/1963 | Raspe et al. | 435/52 |
| 3,388,042 | 6/1968 | Arima et al. | 435/61 |
| 3,734,830 | 5/1973 | Ryu et al. | 435/61 |
| 4,791,057 | 12/1988 | Misaki et al. | 435/26 |

FOREIGN PATENT DOCUMENTS

| | | |
|---|---|---|
| 0108231 | 5/1684 | European Pat. Off. |
| 87/05940 | 10/1987 | WIPO |

*Primary Examiner*—David M. Naff
*Assistant Examiner*—L. Blaine Lankford
*Attorney, Agent, or Firm*—Millen, White, Zelano & Branigan

[57] ABSTRACT

A process for the production of 4-pregnene-3,20-dione and its derivatives of general formula I

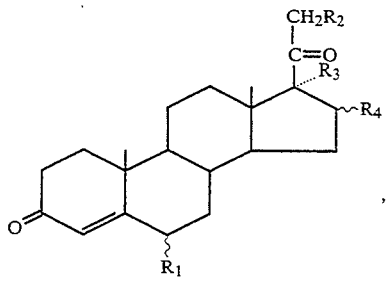

in which
$R_1$ means a hydrogen atom, a fluorine atom or a methyl group,
$R_2$ represents a hydrogen atom or a hydroxy group, and
$R_3$ and $R_4$ together symbolize a carbon-carbon bond or
$R_3$ represents a hydrogen atom, a hydroxy group or an alkanoyloxy group with up to 6 carbon atoms and
$R_4$ means a hydrogen atom or a methyl group, is described, which is characterized in that a pregnane derivative of general formula II

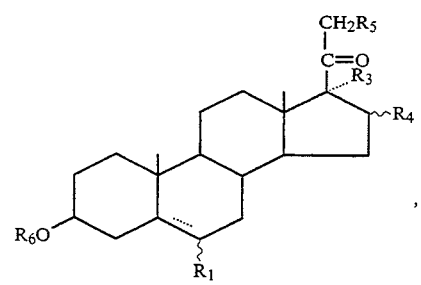

in which $R_1$, $R_3$ and $R_4$ have the above-mentioned meaning,
..... symbolizes a single bond or a double bond,
$R_5$ represents a hydrogen atom, a hydroxy group or an alkanoyloxy group with at most 6 carbon atoms and
$R_6$ means a hydrogen atom or an alkanoyl group with at most 6 carbon atoms, is fermented with a bacterial culture of species Mycobacterium spec. NRRL B-3805.

18 Claims, No Drawings

PROCESS FOR THE PRODUCTION OF 4-PREGNENE-3,20-DIONE AND ITS DERIVATIVES USING MYCOBACTERIUM NRRL B-3805

The invention relates to a process for the production of 4-pregnene-3,20-dione and its derivatives of general formula I

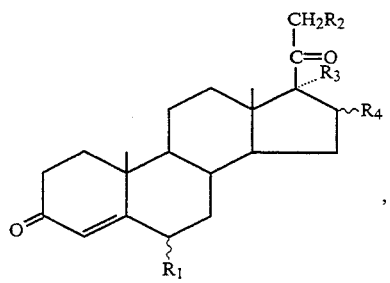

in which
- $R_1$ means a hydrogen atom, a fluorine atom or a methyl group,
- $R_2$ represents a hydrogen atom or a hydroxy group, and
- $R_3$ and $R_4$ together symbolize a carbon-carbon bond or
- $R_3$ represents a hydrogen atom, a hydroxy group or an alkanoyloxy group with up to 6 carbon atoms and
- $R_4$ means a hydrogen atom or a methyl group, characterized in that a pregnane derivative of general formula II

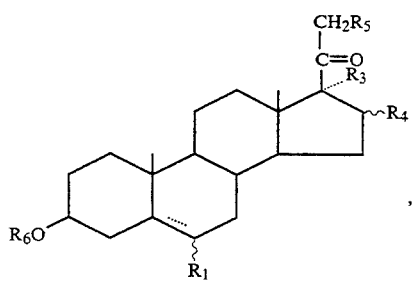

in which $R_1$, $R_3$ and $R_4$ have the above-mentioned meaning,
- ..... symbolizes a single bond or a double bond,
- $R_5$ represents a hydrogen atom, a hydroxy group or an alkanoyloxy group with at most 6 carbon atoms and
- $R_6$ means a hydrogen atom or an alkanoyl group with at most 6 carbon atoms, is fermented with a bacterial culture of species Mycobacterium spec. NRRL B-3805.

This invention is of special importance for the partial synthesis of pharmacologically effective pregnane derivatives from the steroid sapogenins smilagenin and sarsasapogenin widely occurring in nature. It has been known for a long time that these sapogenins can be catabolized relatively simply to $3\beta$-hydroxy-$5\beta$-$3\beta$-hydroxy-$5\beta$-pregn-16-en-20-one or its 3-acetate (U.S. Pat. No. 3,475,464 and Canadian Journ. of Chem., 46, 1968, 733 f). In these compounds, a methyl group in 16-position and/or a methyl group in 17α- and/or 21-position and/or a hydroxy group or acyloxy group in 17α- and/or 21-position can be introduced by methods known in the art, or the 16-double bond of these substances can be hydrogenated. (John Fried and John A. Edwards "Organic Reactions in Steroid Chemistry"; van Nostrand Reinhold Comp. New York, etc. Vol. 1 1972, p. 125 ff, Vol. 2, 1972, p. 075 f and Vol. 2, 1972, p. 162 f and 176 f).

The thus represented pregnane derivatives of general formula IIa

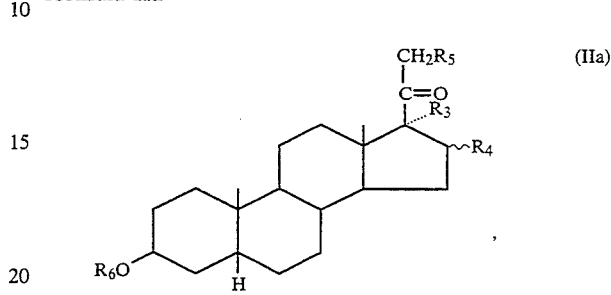

in which $R_3$, $R_4$ and $R_5$ and $R_6$ have the already mentioned meaning, are converted to the corresponding 3-oxo-$\Delta^4$ steroids (U.S. Pat. No. 3,475,464) according to the known prior art in a multistage chemical process which is performed by agents that are harmful to the environment.

In contrast, the process according to the invention makes it possible to convert these compounds to the corresponding 3-oxo-$\Delta^4$ steroids in a one-stage process with good yields being achieved. That this is possible is very surprising to one skilled in the art, since it is known that the microorganism used in this process usually catabolizes the side chains of steroids to the corresponding 17-oxosteroids (GB-A 1,329,287 and U.S. Pat. No. 4,179,336).

The process according to the invention is performed under the same fermentation conditions which are also used with these bacterial cultures in the known microbiological conversions of substrates.

Under the culture conditions usually used for these microorganisms, submerged cultures are cultivated in a suitable nutrient medium with aeration. Then, the substrate (dissolved in a suitable solvent or in emulsified form) is added to the cultures and fermented, until a maximum substrate conversion is achieved.

Suitable substrate solvents are, for example, methanol, ethanol, glycol monomethyl ether, dimethylformamide or dimethylsulfoxide. The emulsification of the substrate can be brought about, for example, by the latter being sprayed in micronized form or dissolved in a water-miscible solvent (such as methanol, ethanol, acetone, glycol monomethyl ether, dimethylformamide or dimethylsulfoxide) under strong turbulence in (preferably decalcified) water, which contains the usual emulsifying aids. Suitable emulsifying aids are nonionogenic emulsifiers, such as, for example, ethylenoxy adducts or fatty acid esters of polyglycols. As suitable emulsifiers, the commercially available wetting agents Tegin ®, Tween ® and Span ® can be mentioned as examples.

The optimum substrate concentration, substrate addition time and fermentation period depend on the type of substrate and microorganism used and the fermentation conditions. These values, as is generally necessary in microbiological steroid conversions, have to be determined in the individual case by preliminary tests, as they are familiar to one skilled in the art.

The process according to the invention can also be performed by using other pregnane derivatives of general formula I than the process of formula Ia, but this brings hardly any advantages according to present knowledge relative to the known microbiological processes.

The following embodiments are used to explain the process according to the invention in more detail.

EXAMPLES

EXAMPLE 1 a) A 2 l Erlenmeyer with 500 ml of sterile nutrient medium containing
1% yeast extract
0.45% $Na_2HPO_4$
0.34% $KH_2PO_4$
0.2% Tween 80 adjusted to pH 6.7
inoculated with an elutriation of a dry culture of Mycobacterium spec. NRRL B-3805 and shaken for 3 days with 180 revolutions per minute at 30° C.

b) 10 g of 3β-acetoxy-5β-16-pregnen-20-one (Canad. J. of Chem., 46, 1968, 734 ff) is ground in a ball mill (PE 075, Netzsch Co., DE-Selb/Bavaria) with corundum balls of a particle size of about 1μ and adjusted with distilled water to an end volume of 500 ml.

c) 50 Erlenmeyers (100 ml) with 20 ml of sterile nutrient medium each containing
2.5 % Cornsteep liquor
0.25 % soybean flour
0.3 % $(NH_4)_2HPO_4$
0.25 % Tween 80 adjusted to pH 6.5
are inoculated with 1 ml of the Mycobacterium-spec.-growing culture each. Then, 3 ml each of the ground suspension produced under b) is added, which corresponds to 0.06 g of 3β-acetoxy-5β -16-pregnen-20-one and is fermented for 120 hours at 30° C. on a rotary shaker with 220 revolutions per minute.

The combined cultures are extracted with methyl isobutyl ketone, mixed with 100 g of activated carbon and filtered on a folded filter. The filtrate is then concentrated by evaporation under vacuum at a maximum of 50° C. in a rotary evaporator and chromatographed on aluminum oxide.

0.7 g of 4,16-pregnadiene-3,20-dione, which is identical with an authentic sample according to HPLC, is thus obtained.

EXAMPLE 2 a) 10 g of 3β-acetoxy-5β-16-pregnen-20-one (Canad. J. of Chem., 46, 1968, 734 ff) is ground as described in example 1b and adjusted to 500 ml with distilled water.

b) Under the conditions of example 1c, 3 ml each of the above-named suspension is added in 50 Erlenmeyer flasks with 100 ml of fermentation culture each, fermented and worked up.

0.75 g of 4-pregnene-3,20-dione, which is identical with an authentic sample according to HPLC, is thus obtained.

EXAMPLE 3 a) 10 g of 3β-hydroxy-5β-pregnan-20-one (Canad. J. of Chem., 46, 1968, 734 ff) is ground as described in example 1b and adjusted to 500 ml with 500 ml of distilled water.

b) Under the conditions of example 1c, 3 ml each of the above-named suspension is added in 50 Erlenmeyer flasks with 100 ml of fermentation culture each, fermented and worked up.

1.0 g of 4-pregnene-3,20-dione, which is identical with an authentic sample according to HPLC, is thus obtained.

EXAMPLE 4 a) 10 g of 21-acetoxy-3β-hydroxy-methyl-5β-pregnan-20-one (DE-B 22 57 132) is ground, as described in example 1 and adjusted to 500 ml with distilled water.

b) Under the conditions of example 1c, 3 ml each of the above-named suspension is added in 50 Erlenmeyer flasks with 100 ml of fermentation culture each, fermented and worked up.

0.2 g of 21-hydroxy-16β-methyl-4-pregnene-3,20-dione, which is identical with an authentic sample according to HPLC, is thus obtained.

What is claimed is:

1. A process for production of 4-pregnene-3,20-diones of formula I

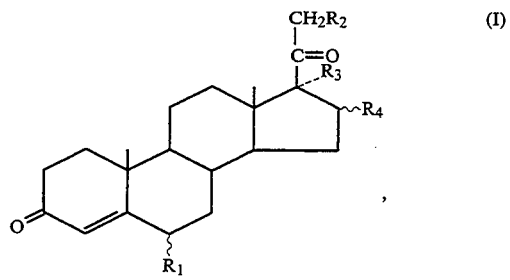

wherein
$R_1$ is hydrogen, fluorine, or methyl,
$R_2$ is hydrogen or hydroxyl and
$R_3$ and $R_4$ together are a carbon-carbon bond or $R_3$ is hydrogen, hydroxy or alkanoyloxy with up to 6 carbon atoms and $R_4$ is hydrogen or methyl,
said process comprising:
fermenting a pregnane or pregnene compound of formula II

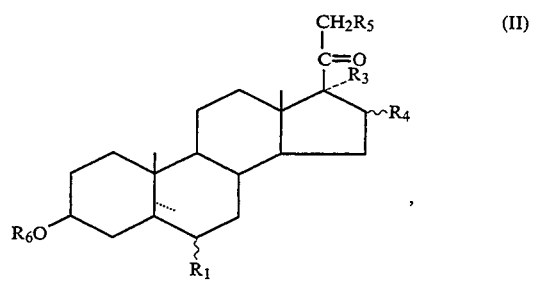

wherein
$R_1$ is hydrogen, fluorine or methyl,
$R_3$ and $R_4$ together are a carbon-carbon bond or $R_3$ is hydroxy or alkanoyloxy with up to 6 carbon atoms and $R_4$ is hydrogen or methyl,
----- is a single bond or a double bond,
$R_5$ is hydrogen, hydroxy or alkanoyloxy with at most 6 carbon atoms, and $R_6$ is hydrogen or alkanoyl with at most 6 carbon atoms, with a bacterial culture of species Mycobacterium spec. NRRL B-3805.

2. A process according to claim 1, wherein said pregnane compound is of formula IIa

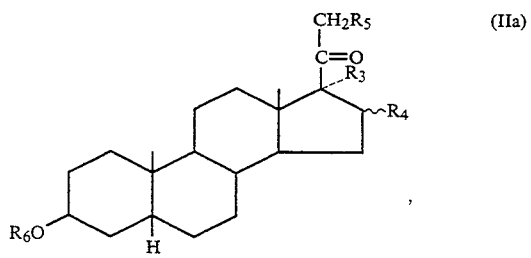

wherein
$R_3$ and $R_4$ together are a carbon-carbon bond or $R_3$ is hydroxy or alkanoyloxy with up to 6 carbon atoms and $R_4$ is hydrogen or methyl,
$R_5$ is hydrogen, hydroxy or alkanoyloxy with at most 6 carbon atoms, and
$R_6$ is hydrogen or alkanoyl with at most 6 carbon atoms.

3. A process according to claim 1, wherein $R_1$ is hydrogen.

4. A process according to claim 1, wherein $R_1$ is fluorine.

5. A process according to claim 1, wherein $R_1$ is methyl.

6. A process according to claim 1, wherein $R_2$ is H.

7. A process according to claim 1, wherein $R_2$ is hydroxy.

8. A process according to claim 1, wherein $R_3$ and $R_4$ together represent a carbon-carbon bond.

9. A process according to claim 1, wherein $R_3$ is H.

10. A process according to claim 1, wherein $R_3$ is hydroxy.

11. A process according to claim 1, wherein $R_3$ is alkanoyloxy with up to 6 carbon atoms.

12. A compound according to claim 1, wherein $R_4$ is H.

13. A compound according to claim 1, wherein $R_4$ is methyl.

14. A process according to claim 1, wherein $R_5$ is H.

15. A process according to claim 1, wherein $R_5$ is hydroxy.

16. A process according to claim 1, wherein $R_5$ is alkanoyloxy with up to 6 carbon atoms.

17. A process according to claim 1, wherein $R_5$ is H.

18. A process according to claim 1, wherein $R_6$ is alkanoyl with up to 6 carbon atoms.

* * * * *

UNITED STATES PATENT AND TRADEMARK OFFICE
CERTIFICATE OF CORRECTION

PATENT NO. : 5,391,484
DATED : February 21, 1995
INVENTOR(S) : Alfred WEBER et al.

It is certified that error appears in the above-indentified patent and that said Letters Patent is hereby corrected as shown below:

Claim 17; column 6, line 24:  Change "$R^5$" to -- $R^6$ --.

Signed and Sealed this

Sixth Day of June, 1995

Attest:

BRUCE LEHMAN

Attesting Officer    Commissioner of Patents and Trademarks